(12) United States Patent
Lim

(10) Patent No.: US 6,984,145 B1
(45) Date of Patent: Jan. 10, 2006

(54) IMPLANTABLE MEDICAL DEVICE CONNECTOR ASSEMBLY WITH SIDE-ACTUATED LEAD BODY AFFIXATION

(75) Inventor: Wisit Lim, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/826,656

(22) Filed: Apr. 16, 2004

(51) Int. Cl.
*H01R 13/58* (2006.01)

(52) U.S. Cl. ............... 439/462; 439/811; 439/909; 439/660

(58) Field of Classification Search ............... 439/811, 439/909, 462, 660
See application file for complete search history.

(56) References Cited

U.S. PATENT DOCUMENTS

| | | | | |
|---|---|---|---|---|
| 4,860,750 A | * | 8/1989 | Frey et al. ............... | 607/37 |
| 5,000,705 A | * | 3/1991 | Kinka et al. ............. | 439/797 |
| 5,261,395 A | | 11/1993 | Oleen et al. ............. | 607/15 |
| 5,413,595 A | | 5/1995 | Stutz, Jr. ............... | 607/637 |
| 5,489,225 A | | 2/1996 | Julian ................... | 439/837 |
| 5,545,188 A | | 8/1996 | Bradshaw et al. ........ | 607/37 |
| 5,766,042 A | | 6/1998 | Ries et al. .............. | 439/668 |
| 5,951,595 A | | 9/1999 | Moberg et al. .......... | 607/37 |
| 6,192,277 B1 | | 2/2001 | Lim et al. ............... | 607/37 |
| 6,339,190 B1 | * | 1/2002 | Chung .................. | 174/50 |
| 6,428,368 B1 | | 8/2002 | Hawkins et al. ........ | 439/909 |
| 6,609,029 B1 | | 8/2003 | Mann et al. ............ | 607/37 |

FOREIGN PATENT DOCUMENTS

WO   WO95/10324   4/1995

* cited by examiner

Primary Examiner—Truc Nguyen

(57) ABSTRACT

A connector assembly releasably affixes a lead on an implantable medical device. The lead includes a lead body. The connector assembly comprises a support, a side clamp defining with the support confronting surfaces configured to receive a proximal end portion of the lead body. A fastener is adapted to be received by the support for urging the side clamp toward the support and for clamping the proximal end portion of the lead body between the confronting surfaces. The fastener may extend through the side clamp and may be threadedly received by the support. Further, the support may carry a retainer for inhibiting the removal of the fastener from the support. The side clamp and the support may define additional confronting surfaces configured to receive a proximal end portion of an additional lead body, the fastener being adapted to urge the side clamp toward the support to clamp the proximal end portion of the additional confronting surfaces. In addition, the connector assembly of the invention may comprise a top clamp defining with the support confronting surfaces configured to receive the proximal end portion of an additional lead body, and a fastener adapted to be received by the support for urging the top clamp toward the support and for clamping the proximal end portion of the additional lead body between the confronting surfaces defined by the top clamp and the support.

27 Claims, 18 Drawing Sheets

IMPLANTABLE MEDICAL DEVICE CONNECTOR ASSEMBLY WITH SIDE-ACTUATED LEAD BODY AFFIXATION

FIELD OF THE INVENTION

The present invention relates generally to electrical connector assemblies forming part of implantable medical devices (IMDs). Such connector assemblies have one or more electrical receptacles each adapted to receive an implantable lead and to connect the lead to electronic circuits within the IMD. More particularly, the invention relates to a side-actuated mechanism forming part of an IMD connector assembly for securely locking the implantable lead within the connector assembly.

BACKGROUND

Although it will become evident to those skilled in the art that the present invention is applicable to a variety of IMDs utilizing pulse generators to stimulate selected body tissue, the invention and its background will be described principally in the context of a specific example of such devices, namely, an implantable cardiac pacemaker and defibrillator unit having a connector assembly defining multiple lead-receiving receptacles. The appended claims are not intended to be limited, however, to any specific example or embodiment described herein.

Cardiac pacemakers, and other implantable stimulation devices such as cardioverters and defibrillators, are hermetically sealed within a housing or casing (sometimes also referred to as a "can") to isolate the electronic circuits contained within the device from the body environment. Such devices require that electrical signals be reliably passed between the hermetically sealed circuitry and external connectors without compromising the hermeticity of the device. Depending on the configuration of the implantable device there may be multiple electrical paths required between the device and its external connectors for delivering, for example, multi-chamber or multi-site stimulation and shock therapy, and for receiving sensed cardiac signals. These paths must be electrically and mechanically integrated with the device to provide a safe, long-term connector assembly that does not compromise the hermetic package.

Typically, a hermetic housing feedthrough electrically couples the electronic circuits contained within the device housing to the connector assembly. The feedthrough extends through the wall of the hermetically sealed casing into the connector assembly so as to couple the electronic circuits within the casing to lead-receiving receptacles within the connector assembly. Each lead has one or more electrical terminals on a proximal end thereof, typically in the form of a pin terminal and one or more conductive ring terminals. Typically, the pin is electrically coupled to a distal tip electrode and is therefore sometimes called the "tip terminal." When the proximal end of the lead is inserted into the lead receptacle of a connector assembly, contacts within the receptacle come into contact with corresponding terminals on the lead so as to couple the lead to the electronic circuits within the implantable stimulation device via the feedthrough assembly. Needless to say, it is imperative that a completely dependable electrical connection be made and retained between the lead terminals and the corresponding connector assembly contacts. At the same time, the connector assembly must be capable of releasing the lead from the lead receptacle during explantation or other subsequent surgical procedure, and must also tightly seal against the entry of body fluids.

It is known in prior art connector assemblies to electrically and mechanically connect the proximal end of the lead within a receptacle of the connector assembly by means of a variety of expedients including captive fastening screw/collet arrangements and setscrews. In those prior art connector assemblies in which the lead is fixed within the lead receptacle using a setscrew, the setscrew is often threaded into an electrical connector block within the connector assembly. When the screw is advanced, it comes into contact with an associated terminal on the proximal end of the lead, mechanically and electrically coupling the lead and the connector assembly. However, the proximal end of a lead is sometimes damaged by an over-tightened setscrew and setscrews have a history of stripping out of the threaded connector block. To minimize or eliminate such problems, setscrews of a certain minimum physical size have been employed. The result is often a protrusion on the side of the connector assembly as the physical size of the pacemaker and its connector assembly is reduced.

A further problem of prior art setscrew type connector assemblies arises from the need to isolate the setscrew and the setscrew block from body fluids. One solution has been to use a silicone seal called a septum. The septum forms an insulation barrier between the setscrew and body fluids. However, the septum must permit a wrench to pass through it so that the screw can be tightened. Frequently, the septum is damaged by the wrench resulting in a loss of the insulation barrier.

U.S. Pat. No. 5,951,595, issued Sep. 14, 1999, and incorporated herein by reference in its entirety, discloses a connector assembly mounted on an implantable cardiac stimulation device having a side-actuated mechanism for fixing and tightly sealing electrical leads inserted into lead receptacles within an IMD connector assembly without the use of setscrews. In the '595 patent, fixing and sealing of the leads is accomplished by compressing resilient lead lock O-ring seals, disposed in annular recesses, with lip portions of a plunger drawn toward a molded support by the actuator mechanism. Other side-actuated mechanisms for lead retention within IMD connector assemblies are disclosed in U.S. Pat. Nos. 6,192,277 and 6,428,368, also incorporated herein by reference in their entireties. These known side-actuated lead locking mechanisms not only provide effective and reliable mechanical and electrical connections but also, for the reasons stated in the '368 patent, are preferred by implanting physicians over front-actuated mechanisms. Nevertheless, these mechanisms tend to be complex and expensive.

Accordingly, it would be desirable to provide a side-actuated connector assembly for securing and locking the proximal end of an implantable stimulation device lead within a lead receptacle that has fewer parts and is less expensive to manufacture.

SUMMARY

What is described herein is a side actuated connector assembly that provides a relatively small number of connector assembly components, thereby simplifying the side-actuated connector assembly concept and reducing manufacturing costs. No special locking seals are required; side clamps engage the lead body to lock the lead in place. The existing seals on the connector assembly provide the fluid seal. Thus, this eliminates lock seals, among other elements.

It will be further appreciated that the connector assembly described herein can be designed to accommodate only a single pacing/sensing and/or cardioverting/defibrillating lead for interaction with the tissue of a single heart chamber, or two leads for dual-chamber stimulation and/or single or dual-chamber sensing, or three, four or even five leads for multi-site or multi-chamber stimulation and/or sensing.

In accordance with one exemplary embodiment, there is provided a connector assembly for releasably affixing a lead on an implantable medical device, the lead including a lead body. The connector assembly comprises a support, a side clamp defining with the support confronting surfaces configured to receive the proximal end portion of the lead body, and a fastener adapted to be received by the support for urging the side clamp toward the support and for clamping the proximal end portion of the lead body between the confronting surfaces. The fastener may extend through the side clamp and may be threadedly received by the support. Further, the support may carry a retainer for inhibiting the removal of the fastener from the support.

In accordance with further illustrative embodiments, the side clamp and the support may define additional confronting surfaces configured to receive the proximal end portion of an additional lead body, the fastener being adapted to urge the side clamp toward the support to clamp the proximal end portion of the additional confronting surfaces. In addition, the connector assembly may comprise a top clamp defining with the support confronting surfaces configured to receive the proximal end portion of an additional lead body, and a fastener adapted to be received by the support for urging the top clamp toward the support and for clamping the proximal end portion of the additional lead body between the confronting surfaces defined by the top clamp and the support.

In accordance with another exemplary embodiment, there is provided a connector assembly for releasably affixing a lead on an implantable medical device, the lead including a lead body having a proximal end portion carrying at least one electrical terminal. The connector assembly preferably comprises a receptacle for receiving the proximal end portion of the lead body, the receptacle carrying an electrical contact positioned to engage the at least one electrical terminal, the receptacle comprising a port defined by a support and a side clamp. A fastener is adapted to be received by the support for urging the side clamp toward the support for clamping the proximal end portion of the lead body within the port. The connector assembly may further comprise a top clamp defining with the support confronting surfaces configured to receive the proximal end portion of an additional lead body, and a fastener adapted to be received by the support for urging the top clamp toward the support and for clamping the proximal end portion of the additional lead body between the confronting surfaces defined by the top clamp and the support.

Pursuant to yet another exemplary embodiment, there is provided a connector assembly for releasably affixing a lead on an implantable medical device, the lead including a lead body having a proximal end portion carrying at least one electrical terminal. The connector assembly comprises a support defining a longitudinal bore. A connector bore assembly carrying an electrical contact extends from the bore. The connector assembly further comprises a side clamp defining with the support a port in alignment with the bore. The bore, the connector bore assembly and the port define a longitudinally extending receptacle for receiving the proximal end portion of the lead body, the electrical contact carried by the connector bore assembly being positioned to engage the at least one electrical terminal on the proximal end portion of the lead body when the proximal end portion of the lead body is inserted into the receptacle. A fastener is adapted to be received by the support for securing the side clamp to the support and for clamping the proximal end portion of the lead body within the port. In accordance with a further aspect of this exemplary embodiment, the side clamp and the support define an additional port in alignment with a corresponding, longitudinally-extending bore defined by the support and with a connector bore assembly extending from the bore. The additional port, the corresponding bore and the corresponding connector bore assembly define an additional longitudinally-extending receptacle for receiving the proximal end portion of an additional lead body, the connector bore assembly carrying an electrical contact positioned to engage an electrical terminal on the proximal end portion of the additional lead body. The fastener is adapted to secure the side clamp to the support to clamp the proximal end portion of the additional lead body within the additional port. Still further, connector assembly may also comprise a top clamp defining with the support an additional port in alignment with a corresponding, longitudinally-extending bore defined by the support and with a connector bore assembly extending from the bore, the additional port, the corresponding bore and the corresponding connector bore assembly define an additional, longitudinally-extending receptacle for receiving the proximal end portion of an additional lead body, the connector bore assembly carrying an electrical contact positioned to engage an electrical terminal on the proximal end portion of the additional lead body. The fastener is adapted to secure the side clamp to the support to clamp the proximal end portion of the additional lead body within the additional port.

According to yet another exemplary embodiment, there is provided a connector assembly for attachment to an implantable medical device, the connector assembly comprising a support comprising a front portion and a rear portion, the front portion comprising opposed, parallel sides. A pair of longitudinally-extending, side-by-side bores are formed in the rear portion of the support. A connector bore assembly is coupled to and extends rearwardly from each of the longitudinally-extending bores, each connector bore assembly carrying at least one electrical contact. The assembly further comprises a pair of opposed side clamps, one of the side clamps and one of the sides of the front portion of the support defining between them a longitudinally-extending port in alignment with one of the pair of longitudinally-extending bores in the rear portion of the support, the other of the side clamps and the other one of the sides of the front portion of the support defining between them a longitudinally-extending port in alignment with the other of the pair of longitudinally-extending bores in the rear portion of the support, each of the sets of aligned ports, bores and connector bore assemblies forming a receptacle for receiving the proximal end portion of the lead body of a medical lead, the at least one electrical contact carried by each of the connector bore assemblies being disposed to make electrical contact with a corresponding electrical terminal on the proximal end portion of said lead body. A fastener extends through each of the side clamps and into the front portion of the support for releasably locking the proximal end portion of a lead body in place within the corresponding port.

In accordance with another embodiment, the connector assembly may further comprise a second pair of longitudinally-extending, side-by-side bores formed in the rear portion of the support, the first mentioned pair of bores and the second pair of bores being arranged in a 4×4 array. A connector bore assembly is coupled to and extends rearwardly from each of the second pair of bores, each of the last mentioned connector bore assemblies carrying at least one electrical contact and one of the side clamps and one of the sides of the front portion of the support defining between them a longitudinally-extending port in alignment with one of the second pair of bores, the other of said side clamps and the other one of the sides of the front portion of the support defining between them a longitudinally-extending port in alignment with the other of the second pair of bores, each of the second mentioned sets of aligned ports, bores and connector bore assemblies forming a receptacle for receiving the proximal end portion of the lead body of a medical lead, the at least one electrical contact carried by each of the second pair of connector bore assemblies being disposed to make electrical contact with a corresponding electrical terminal on the proximal end portion of an associated lead body. The fastener extends through each of the side clamps and into the front portion of the support releasably locking a lead body in place within the associated port in alignment with each of the second pair of bores.

Pursuant to yet another exemplary embodiment, there is provided an implantable medical device comprising a sealed casing, electronic circuitry enclosed within said casing, and a connector assembly attached to the outside of said casing for releasably affixing a lead comprising a lead body having a proximal end portion carrying at least one electrical terminal. The connector assembly comprises a receptacle for receiving the proximal end portion of the lead body, the receptacle carrying an electrical contact positioned to engage the at least one electrical terminal, the electrical contact being electrically coupled to the circuitry. The receptacle comprises a port defined by a support and a side clamp. A fastener is adapted to be received by the support for urging the side clamp toward the support for clamping the proximal end portion of the lead body within the port.

BRIEF DESCRIPTION OF THE DRAWINGS

Further objects, features and advantages will become evident from the detailed description below when read in conjunction with the accompanying drawings in which.

DETAILED DESCRIPTION

Figure 1:
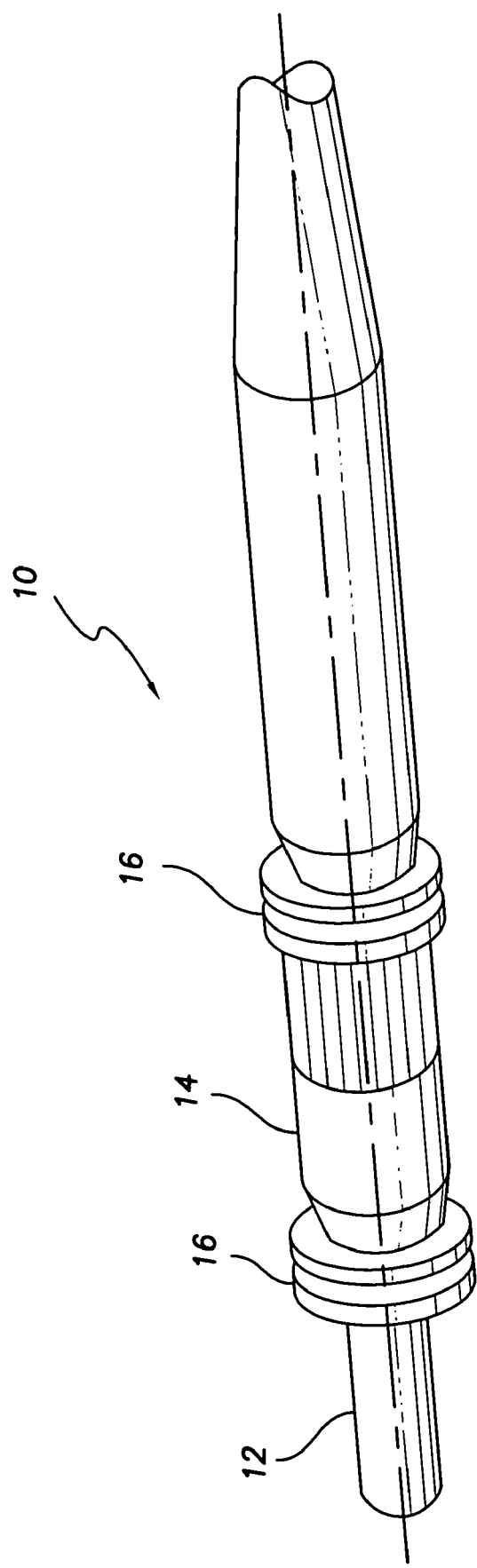
FIG. 1 is a perspective view of the proximal end portion of a conventional/bipolar lead.

FIG. 1 shows a proximal end portion 10 of a conventional transvenous, bipolar pacing lead. The diameter of such a lead may be made sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads having proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consist of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 conforms to the IS-1 standard, comprising a pair of coaxial spaced-apart terminals including a tip terminal 12 and a ring terminal 14. The tip terminal 12 is electrically connected by means of the inner conductor coil to the tip electrode at the distal end of the lead, while the ring terminal 14 is electrically connected to the anodal ring electrode by means of the outer conductor coil. The tip and ring terminals of the lead may each be engaged by a conductive garter spring contact or other resilient electrical contact element carried by a connector assembly as will be described. The proximal end portion further comprises spaced-apart pairs of seal rings 16 for preventing body fluids from reaching the electrical contacts. With the proximal end portion 10 of the lead inserted in a lead receptacle of a connector assembly, the tip and ring terminals 12 and 14 are electrically coupled via the contacts and a feedthrough to the electronic circuits within the hermetically sealed, attached cardiac pacemaker, or other implantable tissue stimulation and/or sensing device.

Figure 2:
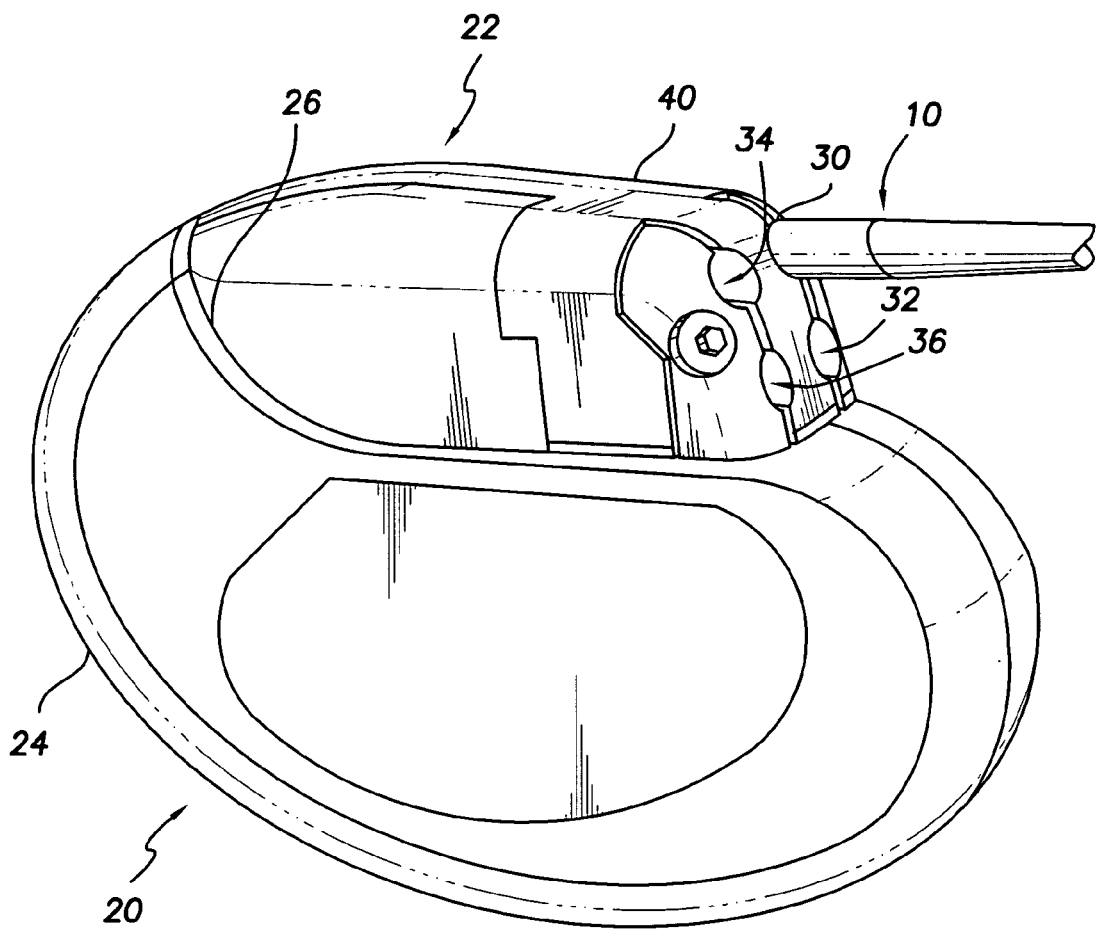
FIG. 2 is a perspective view of a cardiac pacemaker/defibrillator unit including a connector assembly in accordance with one specific, exemplary embodiment.
Figure 3:
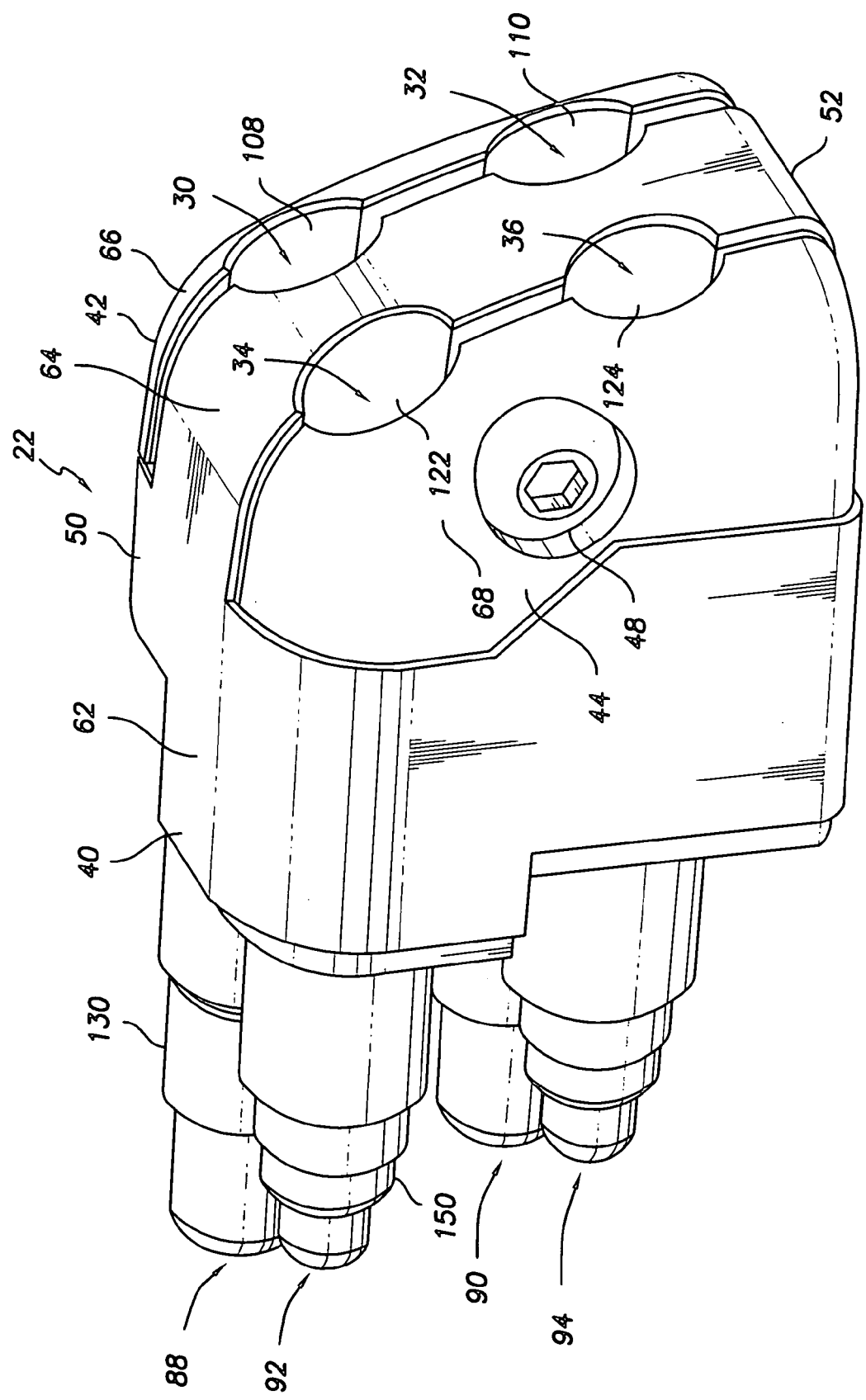
FIG. 3 is a perspective view of the connector assembly depicted in FIG. 2.
Figure 4:
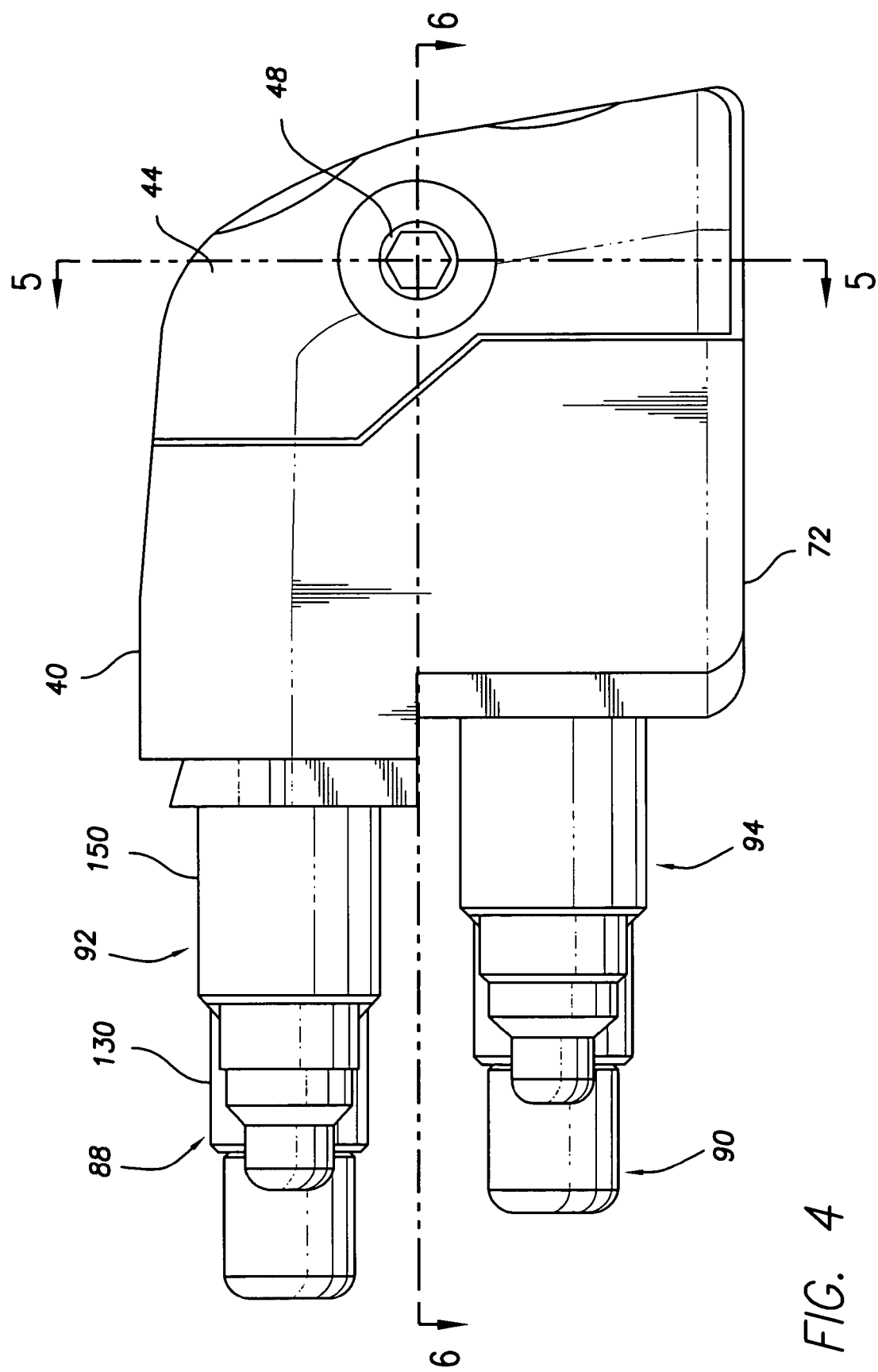
FIG. 4 is a side elevation view of the connector assembly of FIG. 3.

FIG. 2 shows a multi-site or multi-chamber cardiac pacemaker/defibrillator unit 20 incorporating a connector assembly 22 in accordance with one specific, exemplary embodiment. The cardiac pacemaker/defibrillator unit 20 is of a conventional design, including a hermetically sealed can or casing 24 enclosing the electronic components of the pacemaker/defibrillator unit with the connector assembly 22 mounted along a top edge 26 of the unit.

With reference now also to FIGS. 3–10, the connector assembly 22 includes four receptacles comprising a first pair of receptacles 30 and 32 for receiving the proximal ends of conventional bipolar leads and a second pair of receptacles 34 and 36 for receiving the proximal ends of conventional cardioverting and/or defibrillating leads. Stimulation devices employing four leads are sometimes referred to as bi-ventricular, bi-atrial devices, or 4×4 devices because all four chambers of the heart may be stimulated and/or sensed. FIG. 2 shows the proximal end portion 10 of a lead inserted in the bipolar lead receptacle 30.

The connector assembly 22 comprises a support 40, opposed side clamps 42 and 44, and side fasteners 46 and 48 for securing the side clamps to the support 40 to lock the leads in place. The support 40 and side clamps 42 and 44 may be molded of a material such as polysulfone. The support 40 comprises a rear portion 50 and a front portion 52, narrower than the rear portion, defining opposed side recesses 54 and 56 for receiving the side clamps 42 and 44, respectively. The side recesses comprise opposed, parallel side surfaces 58 and 60, respectively. The rear portion 50, the front portion 52 and the side clamps 42 and 44 have curved outer surfaces 62, 64, 66 and 68, respectively, that form a substantially continuous, smooth, outer connector assembly surface when the side clamps are in their fully locked position, as seen, for example, in FIGS. 2–6.

Figure 8:
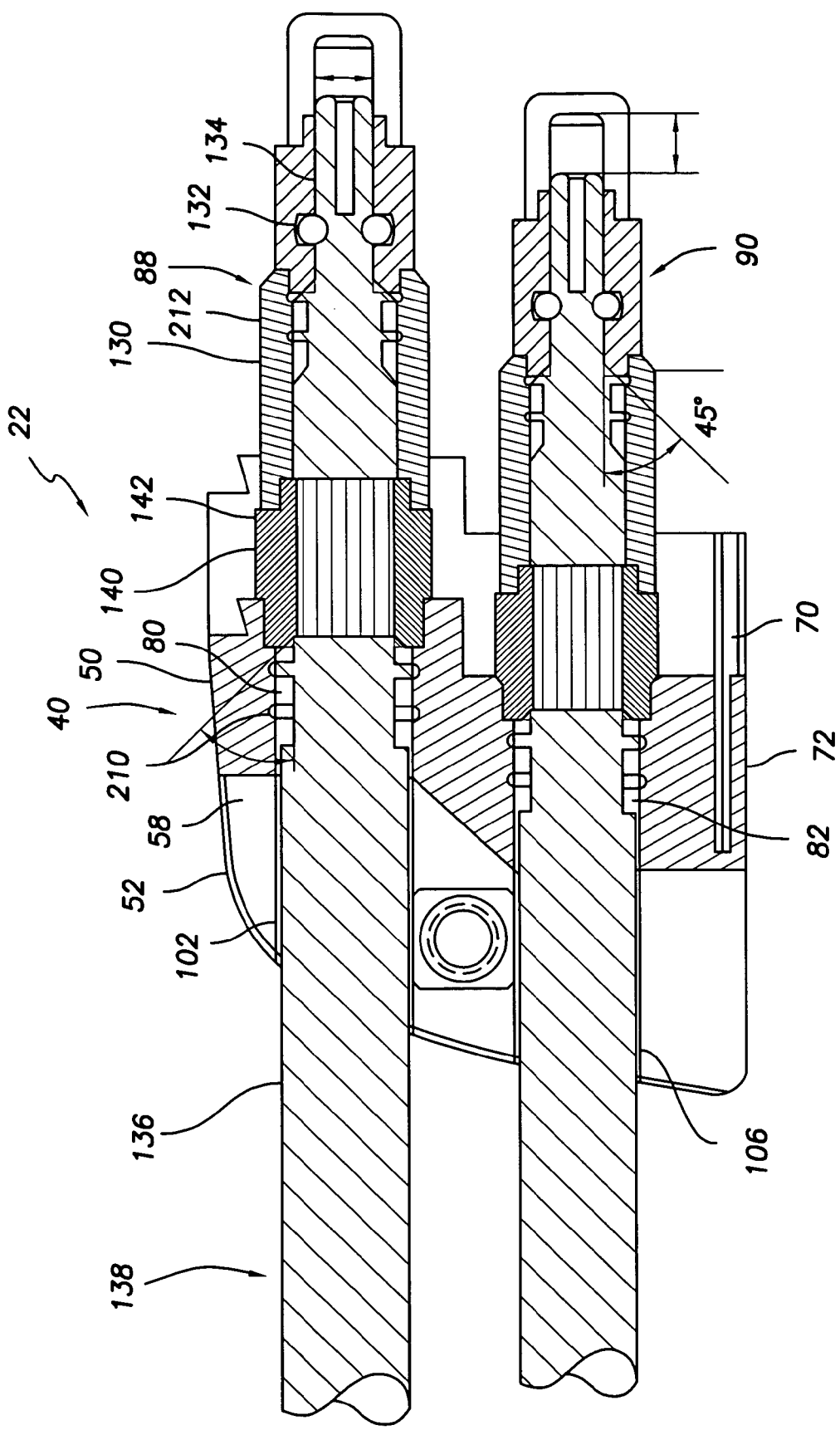
FIG. 8 is a side elevation view, in cross section, of the connector assembly of FIGS. 3–5 as seen along the line 8—8 in FIG. 5.
Figure 9:
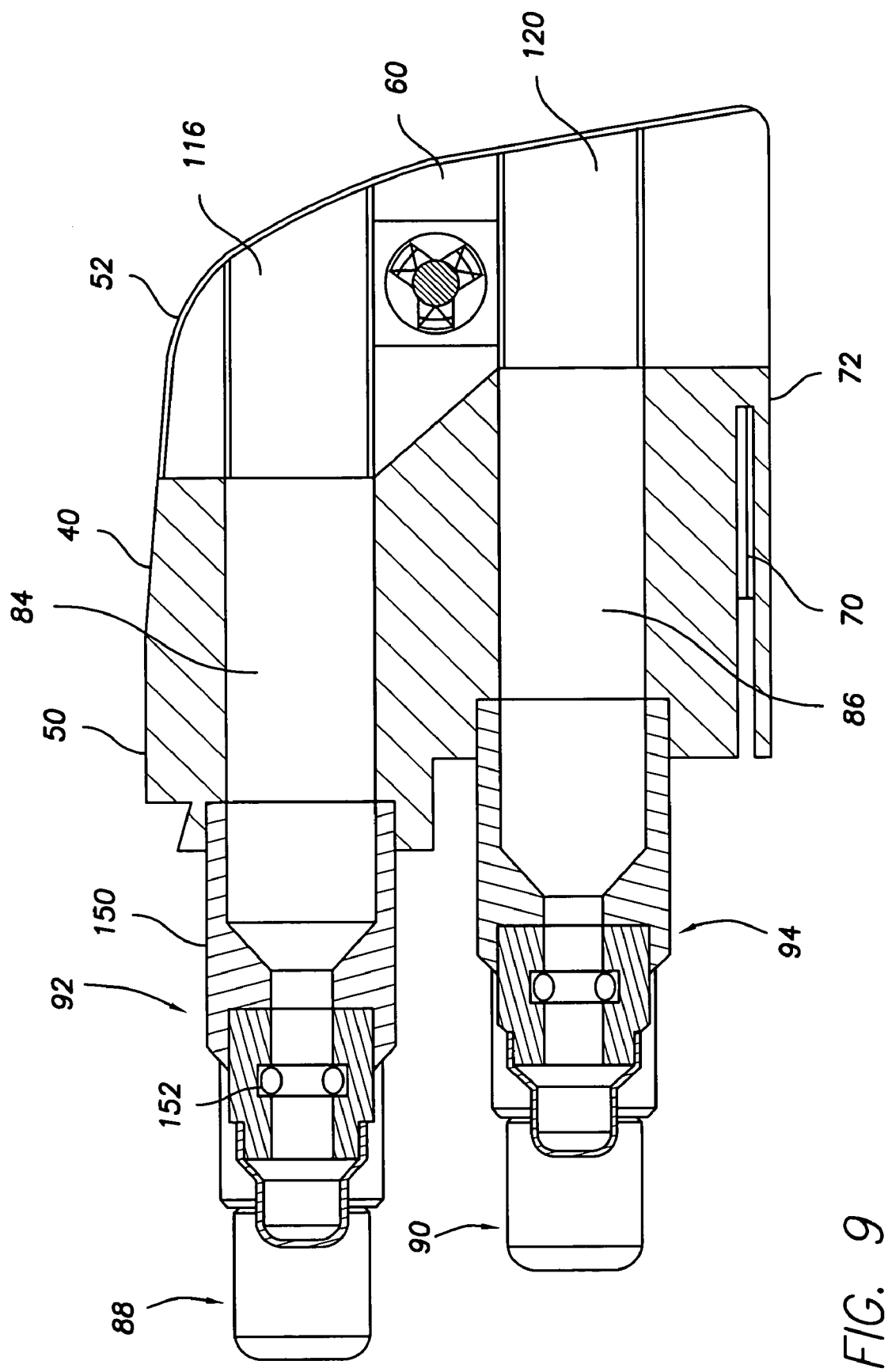
FIG. 9 is a side elevation view, in cross section, of the connector assembly of FIGS. 3–5 as seen along the line 9—9 in FIG. 5.
Figure 10:
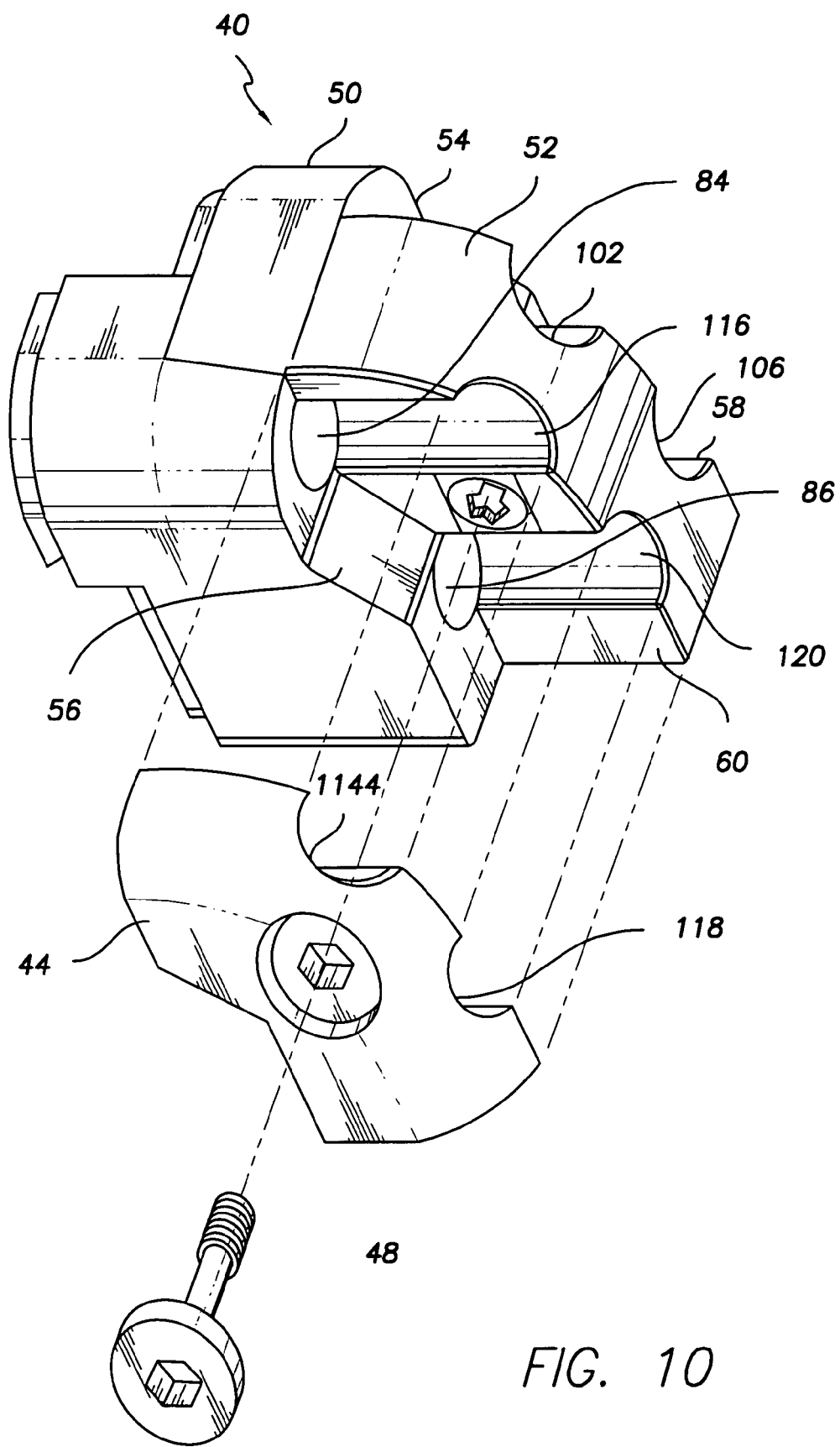
FIG. 10 is an exploded, perspective view of the molded support and one of the side clamps forming part of the connector assembly.

As shown, for example, in FIGS. 8 and 9, the connector assembly 22 includes a conventional dovetail mount 70 on the bottom 72 of the molded support 40 to facilitate mounting of the connector assembly on the top of the pacemaker/defibrillator unit 20, in a manner well known in the art.

The rear portion 50 of the support 40 defines four parallel, longitudinally extending bores 80, 82, 84 and 86. Extending rearwardly from the bores 80 and 82 and press fit therein are connector bore assemblies 88 and 90 incorporating contacts conforming to a standard such as the IS-1 standard. Extending rearwardly from the bores 84 and 86 are connector bore assemblies 92 and 94 incorporating contacts conforming to a standard such as the DF-1 standard. The side clamp 42 and the side surface 58 of the front portion 52 of the support are provided with confronting longitudinally extending surfaces preferably in the form of grooves or channels 100/102 and 104/106 defining between them longitudinally-extending ports 108 and 110 in alignment with the bores 80 and 82 in the rear portion 50 of the support 40. In the embodiment under consideration, the channels may be symmetrical about a vertical interface plane 112. The aligned port 108, bore 80 and connector bore assembly 88 form the receptacle 30 for receiving the proximal end portion of a bipolar lead, while the aligned port 110, bore 82 and connector bore assembly 90 form the receptacle 32 for the proximal end portion of another bipolar lead. In similar fashion, the side clamp 44 and the side surface 60 of the front portion of the support are provided with confronting longitudinally-extending grooves or channels 114/116 and 118/120 defining between them longitudinally-extending ports 122 and 124 in alignment with the bores 84 and 86 in the rear portion 50 of the support 40. These channels may be symmetrical about a second vertical interface plane 126. The aligned port 122, bore 84 and connector bore assembly 92 form the receptacle 34 for receiving the proximal end portion of a cardioverter/defibrillator lead. Similarly, the aligned port 124, bore 86 and connector bore assembly 94 form the receptacle 36 for receiving the proximal end portion of a second cardioverter/defibrillator lead.

FIG. 8 shows details of the connector bore assemblies 80 and 82 for receiving the proximal ends of a pair of bipolar leads. As noted, the contact arrangement illustrated by way of example conforms to the IS-1 standard and it will be evident that other arrangements may be utilized.

The connector bore assembly 80, taken as representative, comprises a multi-section, generally tubular structure 130 carrying a first resilient electrical contact in the form of a first garter spring 132 for engaging a pin terminal 134 on the proximal end portion 136 of a lead 138. Similarly, a second resilient electrical contact in the form of a second garter spring 140 engages a ring terminal 142 on the proximal end portion 136 of the lead 138. In a fashion well known in the art, the garter spring contacts 132 and 140 are electrically connected to the pins of a feedthrough assembly (not shown) in turn coupled to the pacing/sensing electronic circuitry within the hermetically sealed housing of the implantable medical device. The structure of the connector bore assembly 82 is substantially the same as that of the assembly 80.

With reference to FIG. 9, each of the connector bore assemblies 84 and 86 is configured to receive the proximal end portion of a defibrillator lead. Representative assembly 84 comprises a multi-section, generally tubular structure 150 carrying a resilient electrical contact in the form of a garter spring 152 for engaging the pin terminal on the proximal end of the defibrillator lead (not shown). The garter spring contact 152 is electrically connected in conventional fashion to the defibrillating electronic circuitry within the sealed housing via an appropriate feedthrough assembly (not shown). The structure of the assembly 86 is substantially the same as that of the assembly 84.

Figure 5:
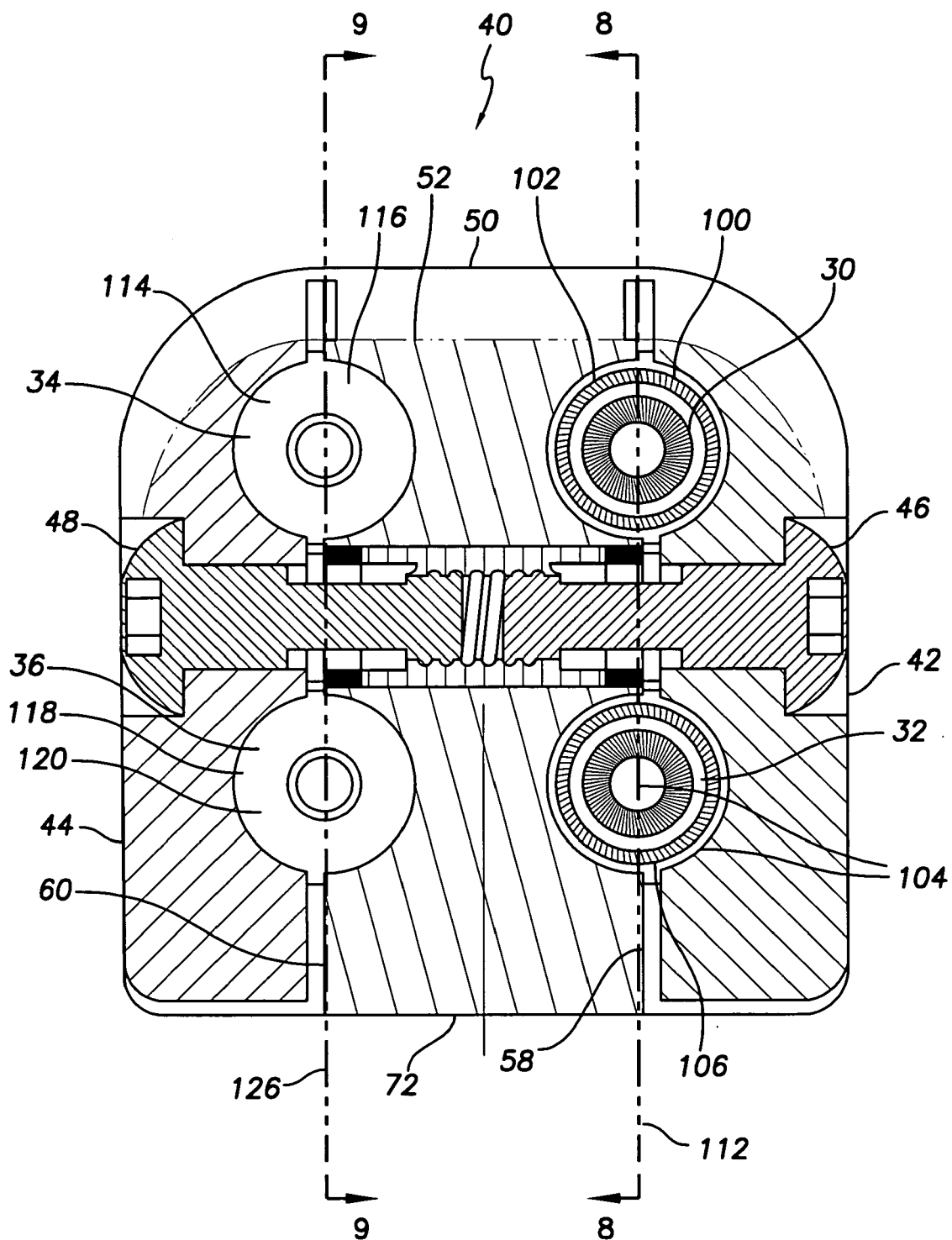
FIG. 5 is a front end elevation view, in cross section, of the connector assembly of FIGS. 3 and 4 as seen along the line 5—5 in FIG. 4.
Figure 6:
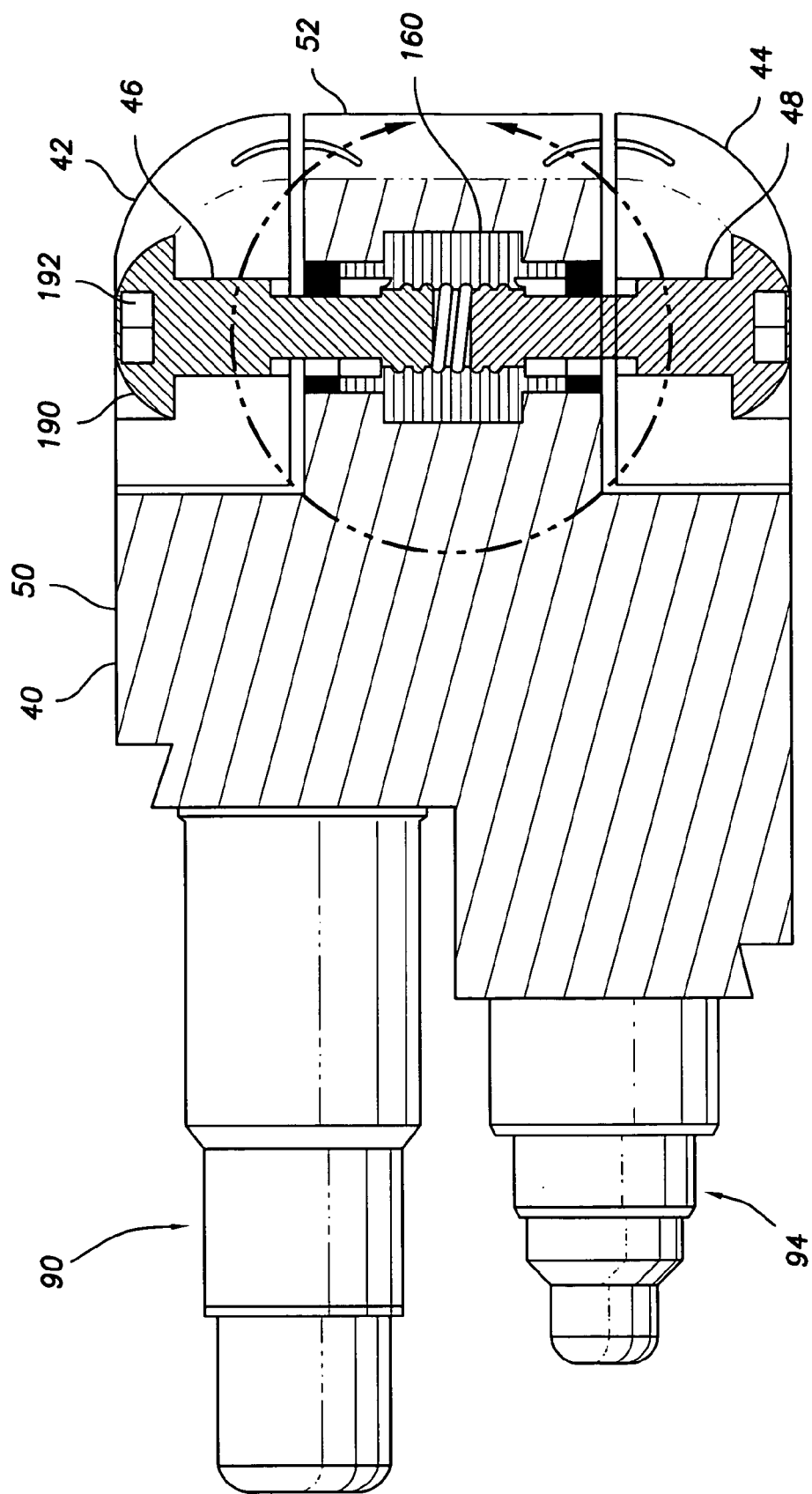
FIG. 6 is a top plan view, in cross section, of the connector assembly of FIGS. 3 and 4 as seen along the line 6—6 in FIG. 4.
Figure 7:
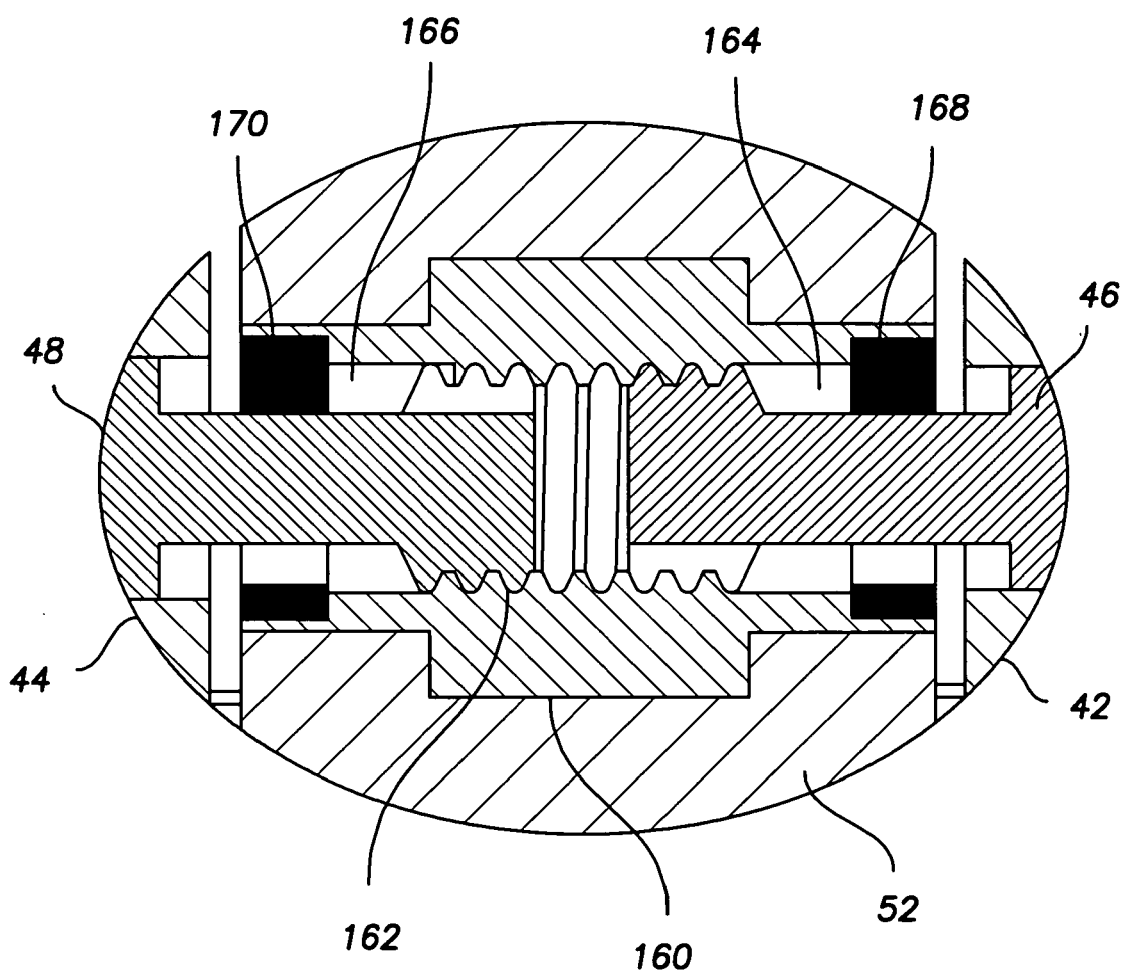
FIG. 7 is an enlargement of a portion of the cross section view of FIG. 6.
Figure 11:
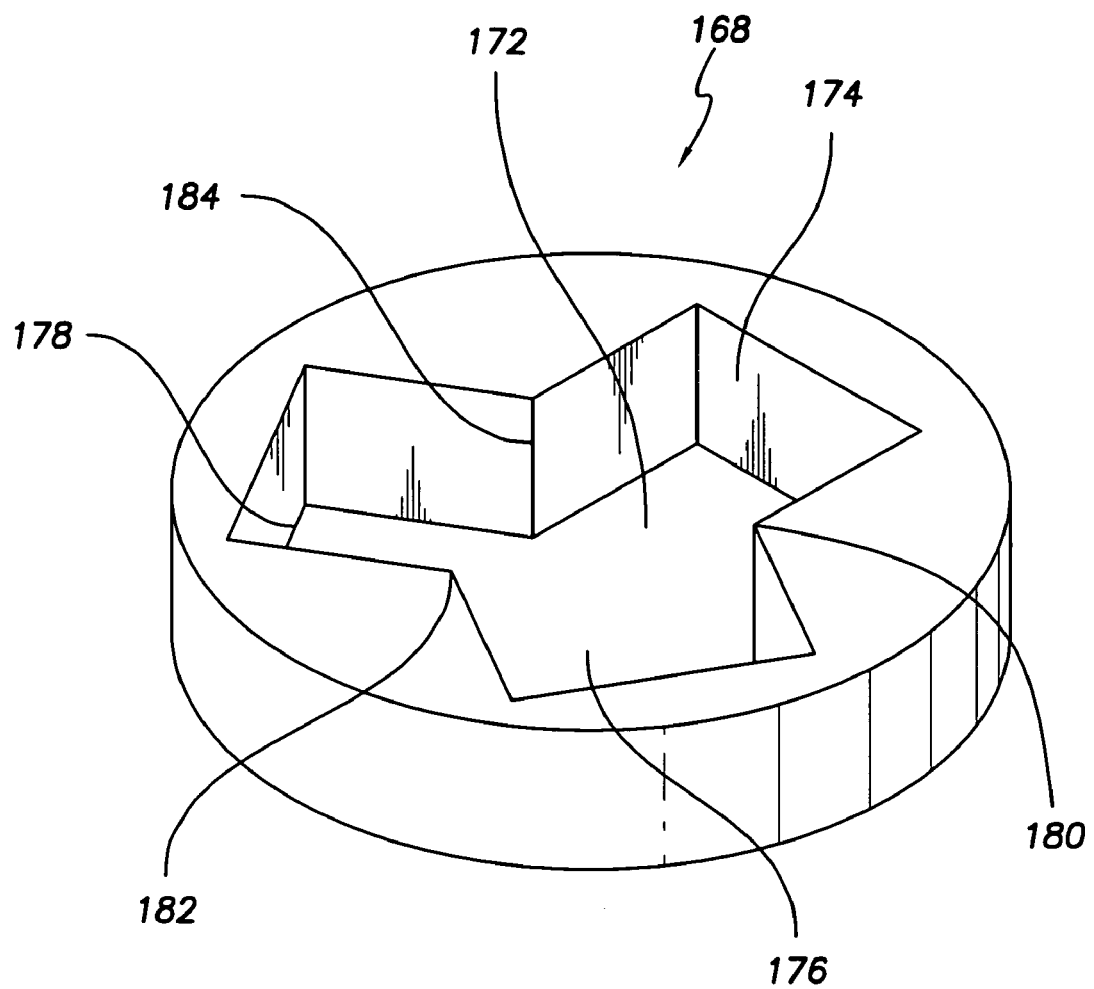
FIG. 11 is a perspective view of a disk insert forming part of the connector assembly.

With reference to FIGS. 5, 6 and 7 the narrow, front portion 52 of the support 40 includes a transversely extending insert 160, preferably metal, co-molded with the support 40 so as to be securely affixed thereto and having a central threaded region 162. The outer extremities of the insert have counterbores 164 and 166 receiving fastener retainer disks 168 and 170, respectively, as best seen in FIGS. 5, 6, 7 and 10 that are held in place within the counterbores by welding or by an appropriate bonding agent. As shown in the detail of FIG. 11 showing retainer disk 168, each disk includes a central cutout 172 comprising three equiangularly spaced rectangular portions 174,176 and 178 intersecting at three apexes 180,182 and 184.

Figure 12:
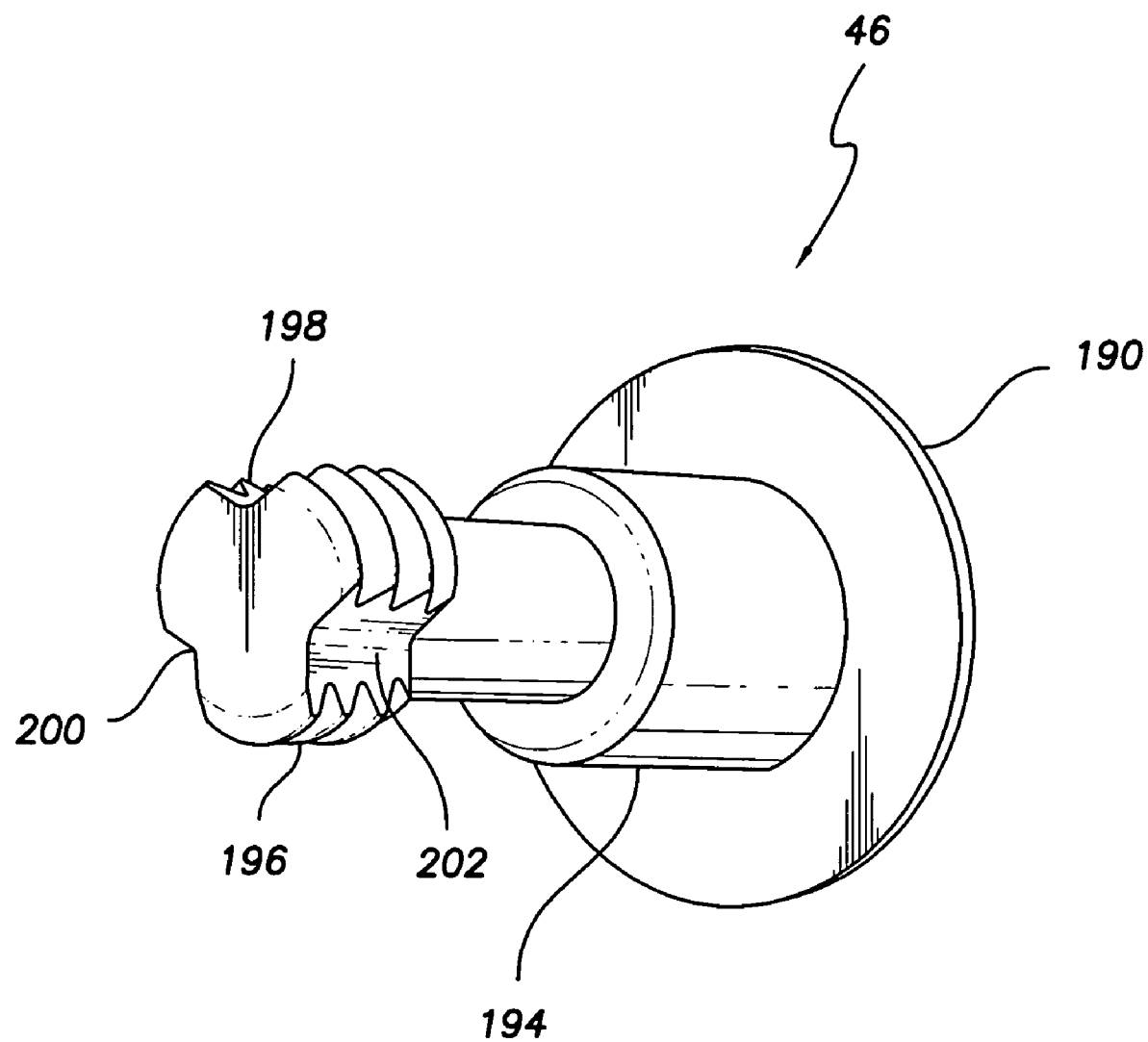
FIG. 12 is a perspective view of a side fastener forming part of the connector assembly.

Turning again to FIGS. 5, 6, 7 and 10, and also to FIG. 12, there is shown in greater detail the side fastener 46, taken as representative, for securing the side clamp 42 to the support 40 and for thereby locking in place the lead ends received by the ports 108 and 110. The side fastener 46 comprises a screw including an enlarged head 190 defining a central hexagonal recess 192 for receiving a hex tool, a stepped shank 194 and a threaded inner end 196. The threaded end 196 includes three equiangularly spaced notches 198, 200 and 202 permitting the segmented threaded end 196 of the fastener to be inserted through the cutout 172 in the associated disk 168 carried by the insert 160. As best seen in FIGS. 5, 6 and 7, the threaded end 196 of the side fastener is received by the internal threaded region 162 of the insert. Tightening of the fastener 46 clockwise urges the side clamp 42 toward the side surface 58 of the support 40 so that with leads inserted in the ports of the support assembly the proximal end portions of the lead bodies will be securely clamped within the confronting channels in the side clamps and support. The side clamp 42 and the side fastener 46 may be loosely preassembled prior to insertion of the leads into the ports, that is, the support assembly need not be disassembled prior to its use. The length of the threaded end 196 of the fastener 46 is less than the length of the portion of the counterbore 164 between the retainer disk 168 and the central threaded region 162 of the insert 160 so that when the threaded end 196 of the fastener 46 is within that portion of the counterbore 164 the fastener is free to rotate. The disk 168 prevents removal of the side fastener 46 and side clamp 42 from the support so long as the spaced notches 198, 200 and 202 on the fastener are out of alignment with the apexes 180, 182 and 184 on the retainer disk 168. The side fastener 48 operates in association with the side clamp 44, the insert 160, and the retainer disk 170 in the same fashion.

To positively lock a lead in place within the connector assembly, the associated side fastener is turned clockwise by means of a torque-limiting wrench until the torque wrench clicks indicating that the appropriate predetermined level of torque has been applied to securely lock the lead in the connector bore assembly without overtightening. As best seen in FIG. 8, annular seals 210 and 212 on the proximal ends of the bipolar pacing leads provide the necessary sealing against the entry of body fluids. Similar seals on the cardioverter/defibrillator leads (not shown) engage the walls of corresponding connector bore assemblies shown in FIG. 9. Special locking seals such as those used in prior connector assemblies are thereby eliminated. To remove the leads, the side fasteners 46 and 48 are simply turned counterclockwise thereby releasing the side clamps 42 and 44 and permitting withdrawal of the leads from the ports. The side clamps 42 and 44 will remain coupled to the support by the side fasteners so long as their notches remain out of alignment with the apexes on the retainer disk. To separate a side clamp from the support, the side fastener is rotated to bring the grooves and apexes into alignment permitting the side fastener to be withdrawn from the support.

With reference to FIGS. 13–16, there are shown in simplified, schematic form, rear elevation views, in cross section, of four connector assemblies in accordance with alternative embodiments.

Figure 13:
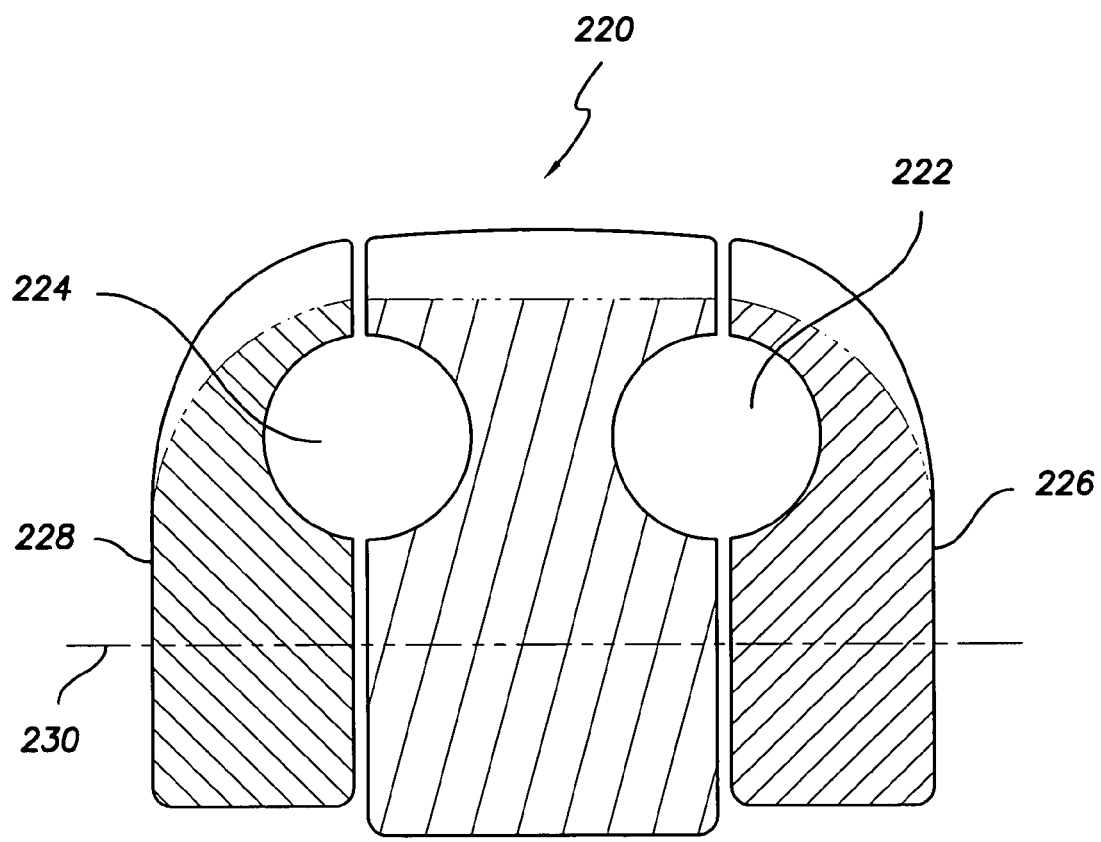
FIGS. 13–16 are simplified, front end elevation views, in cross section, of four alternative embodiments.

FIG. 13 depicts a connector assembly 220 defining two lead-receiving ports 222 and 224 arranged side by side. In the fashion already described, opposed side clamps 226 and 228 along with associated side fasteners (not shown but disposed along a line 230) lock the leads in place.

Figure 14:
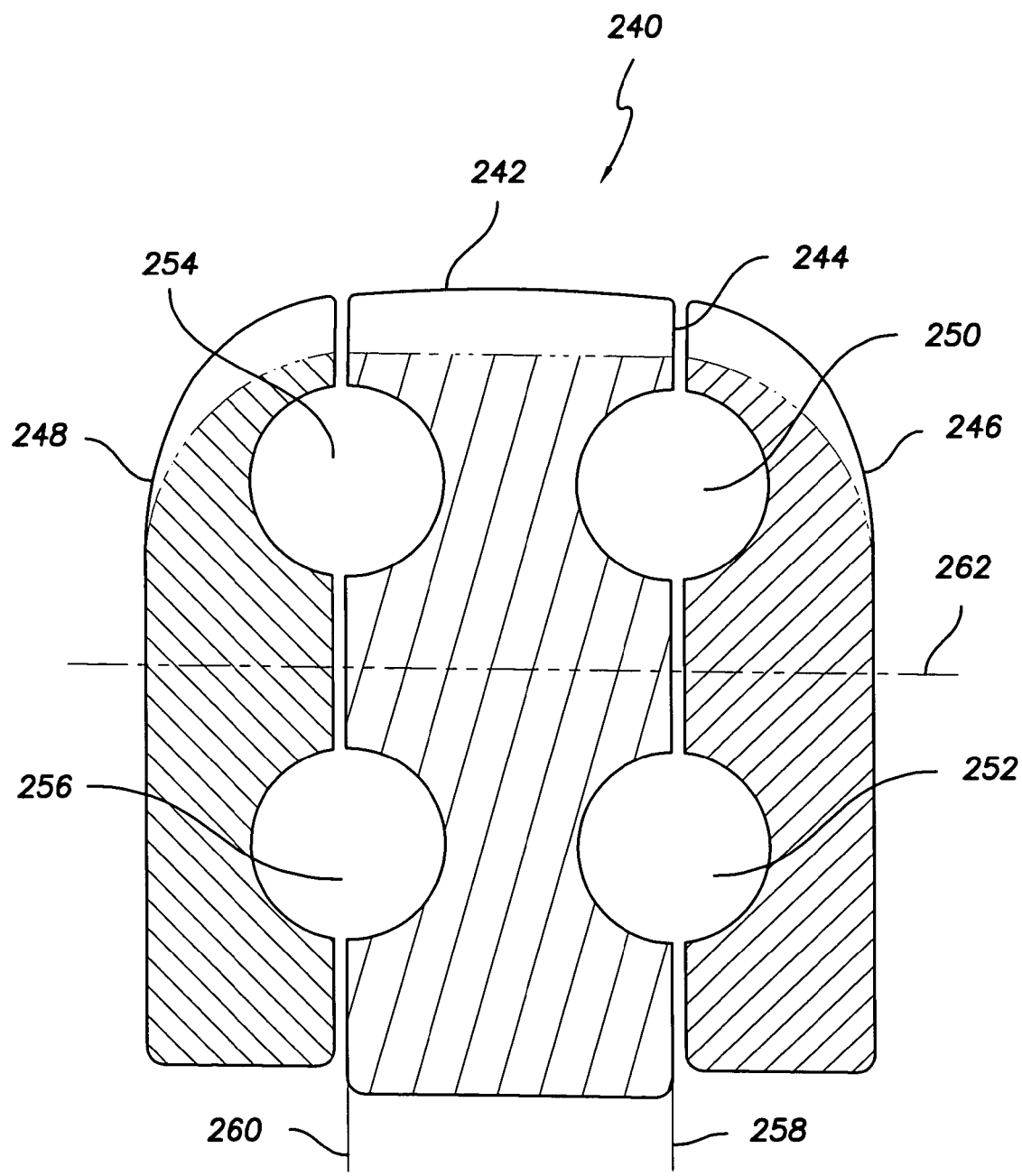

With reference to FIG. 14, there is shown in simplified form a portion of a connector assembly 240 in accordance with yet another alternative embodiment. The connector assembly of FIG. 14 comprises a 4×4 structure of the kind shown and described in connection with the first embodiment. The connector assembly 240 comprises a support 242 with a forwardly extending narrow portion 244 and side clamps 246 and 248. The support and side clamps shown in FIG. 14 define between them lead-receiving ports 250, 252, 254 and 256 defined, as before, by parallel confronting channels in the front portion of the support and the side clamps. The difference, however, is that in FIG. 14, the ports are arranged asymmetrically relative to vertical interface planes 258 and 260. More specifically, the portion of each of the ports in the support is defined by a larger channel than the channel defined by the side clamp. Everything else is similar to the embodiments previously described with side fasteners and an associated threaded insert (not shown) being arranged along a horizontal line 262.

Figure 15:
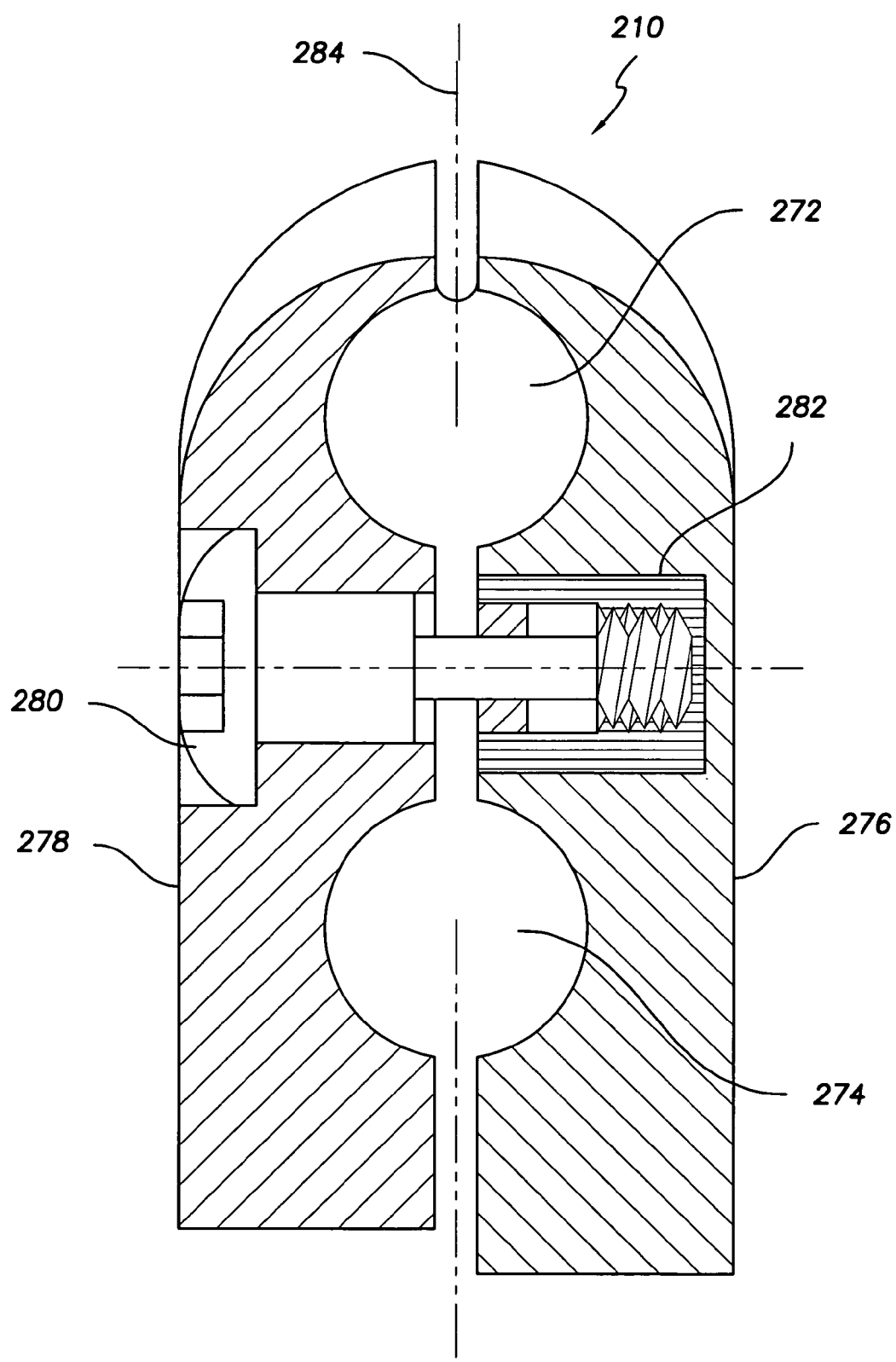

With reference to FIG. 15, there is shown in simplified, schematic form, a connector assembly 270 in accordance with yet another embodiment. In this case, the connector assembly 270 includes two parallel ports 272 and 274 vertically spaced apart with each configured to receive the proximal end of a bipolar pacing and/or sensing lead or a cardioverting and/or defibrillating lead. The connector assembly 270 of FIG. 15 includes a support 276, a single side clamp 278, and a side fastener 280 and associated threaded insert 282 along the lines already described for securing the side clamp to the support. The insert 282 may essentially comprise one-half of the insert 160 shown in FIG. 7. Longitudinally extending, parallel, confronting channels in the support and side clamp define the ports that are symmetrically disposed about a central vertical interface plane 284.

Figure 16:
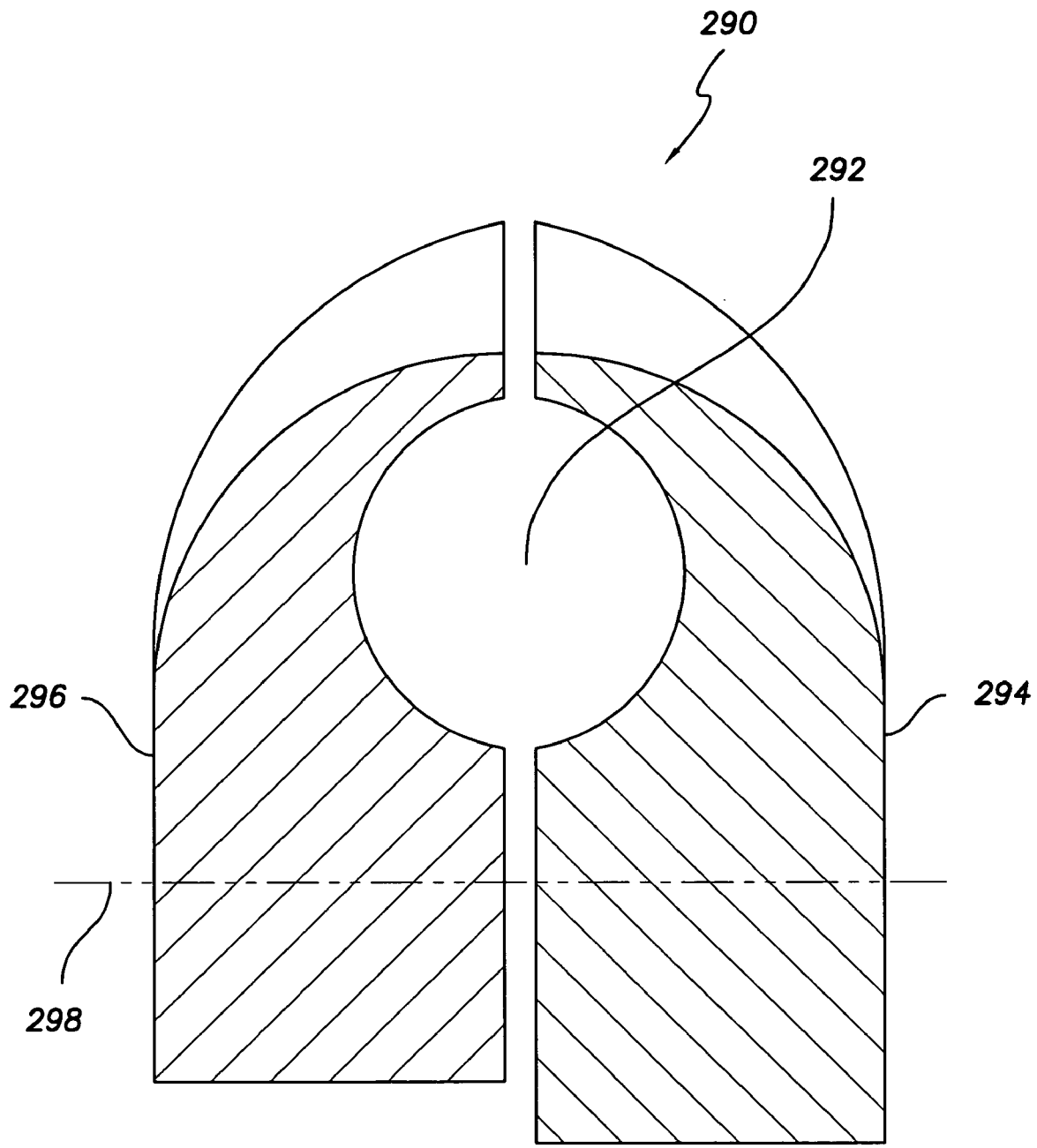

FIG. 16 shows a connector assembly 290 in accordance with still a further alternative embodiment comprising a single port 292 for receiving the terminal-bearing proximal end portion of a conventional bipolar lead or a conventional cardioverting and/or defibrillating lead. The connector assembly 290 comprises a support 294, a single side clamp 296 and an associated side fastener and insert (not shown but extending along the line 298) for securing the side clamp to the support to lock a lead in place.

Figure 17:
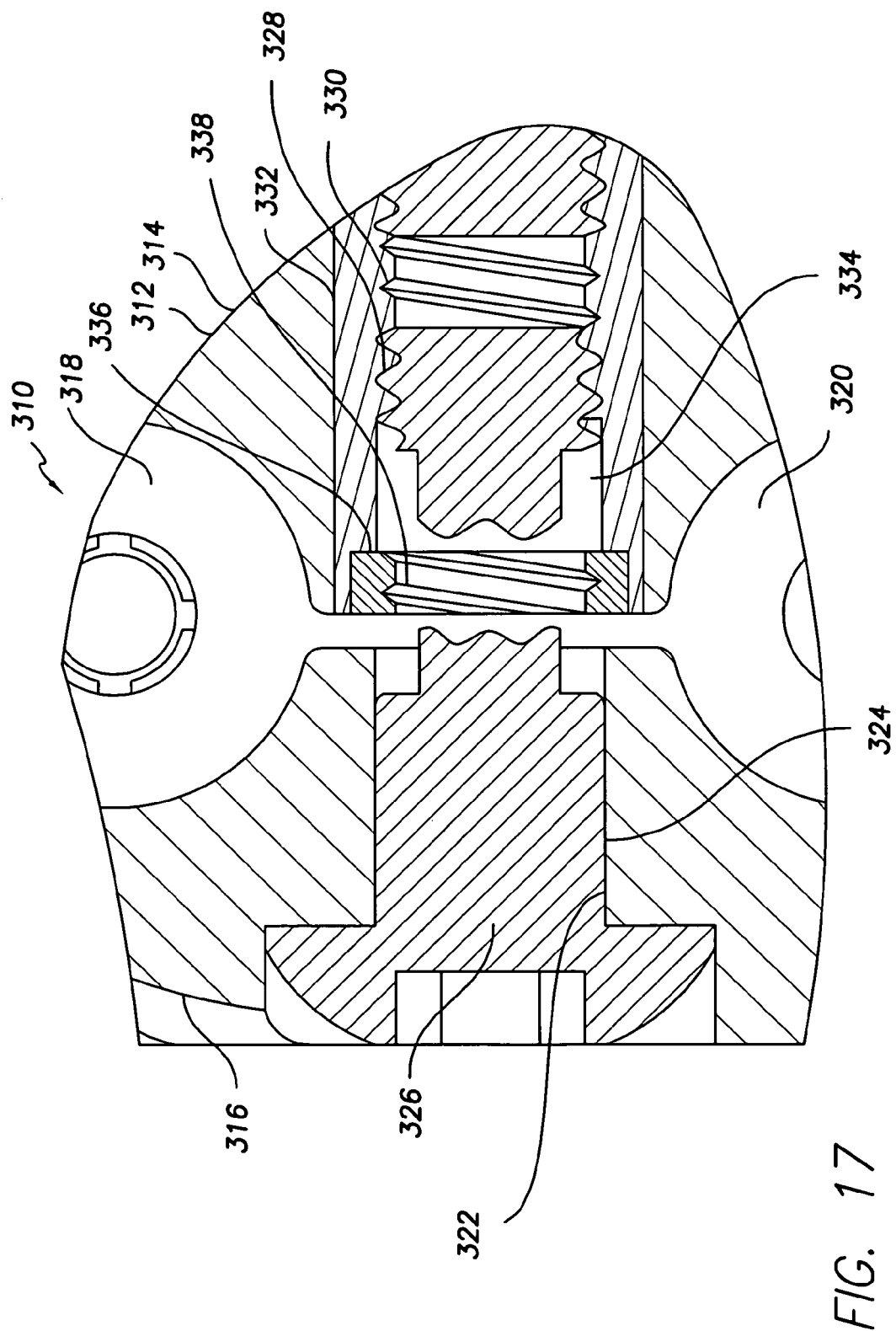
FIG. 17 is a partial front end elevation view, in cross section and partly broken away, of yet another alternative embodiment.

FIG. 17 is an enlarged front end elevation view, in cross section and partly broken away, of a portion of a 4×4 connector assembly 310 in accordance with yet another alternative embodiment. As before, the connector assembly 310 comprises a support 312 preferably having a narrow front portion 314 cooperating with a pair of side clamps, part of one of which (side clamp 316) is shown. As before, the front portion 314 of the support 312 and the side clamp 316 are channeled so as to define between them a pair of lead body-receiving ports 318 and 320. The side clamp 316 includes a transversely extending aperture 322 for receiving the stepped shank 324 of a side fastener 326. The side fastener 326 has a threaded end 328 adapted to be received by a threaded central portion 330 of a metallic insert 332 co-molded with the support 312 so as to be securely affixed therein. The insert 332 includes a stepped counterbore 334 carrying at its outer extremity a fastener retainer ring 336. The retainer ring has internal threads 338 matching those on the threaded end 328 of the side fastener 326. The retainer ring 336 is preferably metallic and is preferably secured to the insert 332 by means of a weld although it will be evident that other bonding techniques may be employed. Still further, it will be evident that instead of using a separate retainer ring, the threads 338 may be formed as an integral part of the insert 332. The length of the threaded end 328 of the fastener 326 is less than the length of the portion of the counterbore 334 between the retainer ring 336 and the threaded portion 330 of the insert 332 so that when the threaded end of the fastener is within that portion of the counterbore 334, the fastener is free to rotate. Installation of the side clamp 316 on the support 312 is accomplished by passing the threaded end 328 of the fastener 326 through the aperture 322 in the side clamp 316. Clockwise rotation of the fastener 326 moves the threaded end of the fastener through the correspondingly threaded retainer ring 336 and into the counterbore 334 of the insert within which the threaded end of the fastener is free of the retainer ring threads enabling the fastener to be further advanced and threadedly secured to the threaded central portion 330 of the insert. Tightening of the fastener 326 firmly clamps the lead body of a medical lead within each of the ports 318 and 320. To unlock the lead bodies permitting them to be withdrawn from the connector assembly, the fastener 326 is unscrewed resulting in its threaded end 328 entering the counterbore 334 of the insert. The side clamp 316 remains coupled to the support unless an intentional effort is made to remove the fastener from the support by rotating the fastener counterclockwise to enable the threaded end of the fastener to engage the threads on the retainer ring and to be thereby unscrewed therefrom. This embodiment provides a more secure connection between the side fastener and the support in contrast to the first embodiment in which unintentional alignment of the grooves in the threaded end of the fastener with the apexes in the retainer disk will cause the fastener and support to separate. It will be evident that in the embodiment of FIG. 17, the grooves may be eliminated and continuous threads provided on the side fastener.

Figure 18:
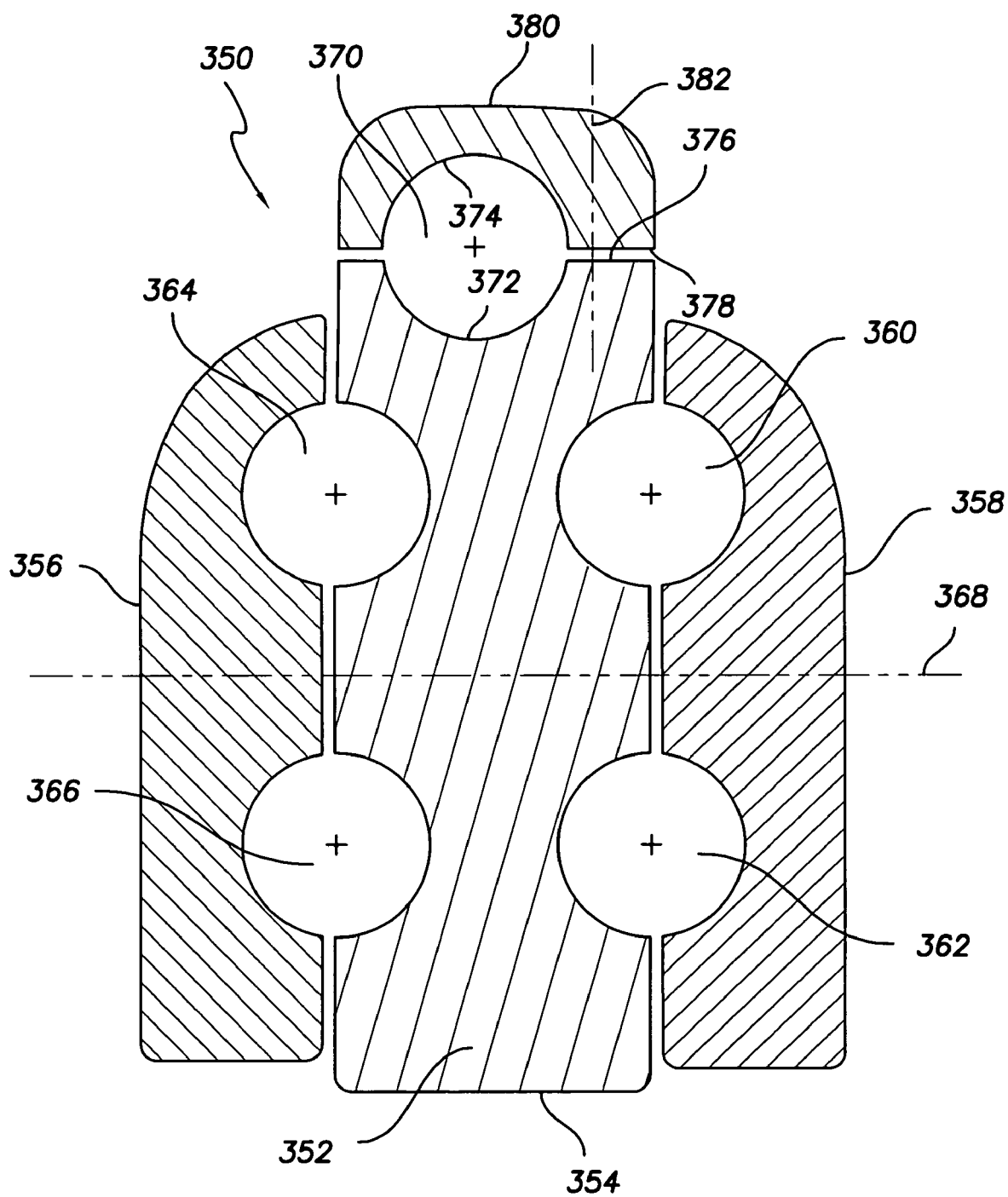
FIG. 18 is a simplified, front end elevation view, in cross section, of yet another alternative embodiment.

FIG. 18 shows in simplified form a cross-section of a portion of a connector assembly 350 in accordance with still a further alternative embodiment. The connector assembly 350 basically comprises a 4×4 structure of the kind shown and described in connection with the embodiment of FIGS. 2–10. Accordingly, the connector assembly 350 comprises a support 352 with a forwardly extending, narrow portion 354 and opposed side clamps 356 and 358. The support 352 and side clamps 356 and 358 define between them four lead-receiving ports 360, 362, 364 and 366 for receiving the proximal end portions of lead bodies and defined, as before, by parallel confronting channels formed in the front portion of the support 352 and in the side clamps 356 and 358. As in the embodiment of FIGS. 2–10, fasteners (not shown) adapted to be received by the support, for example, by an associated threaded insert (not shown) comolded with the support, may be arranged along a horizontal line 368. Added to the basic 4×4 connector assembly 350 is a fifth or top lead-receiving port 370 for receiving the proximal end portion of a lead body and defined by parallel confronting channels 372 and 374 formed, respectively, in a top surface 376 of the support 352 and a bottom surface 378 of a top clamp 380. The securement of the top clamp to the support may be along the lines of the embodiment shown in FIG. 16 with a top fastener and associated half threaded insert (not shown) disposed along a vertical line 382. As described above, the ports 360, 362, 364, 366 and 370 may be associated with corresponding bores and connector bore assemblies to define lead body receptacles each carrying one or more electrical contacts positioned to be engaged by electrical terminals on the proximal end portion of a lead body. The connector assembly 350 is typically incorporated in an IMD designed for multi-site or multi-chamber stimulation and/or sensing. Thus, by way of example only, the right hand ports 360 and 362 and associated receptacles may be configured to receive left ventricle and right ventricle pacing leads, while the left hand ports 364 and 366 and associated receptacles may be configured to receive cardioverting and/or defibrillating leads for stimulating the SVC and the right ventricle. The receptacle associated with the top port 370 may be configured to receive a lead for pacing the right atrium. Other combinations of lead functions are, of course, possible. The IMD with which the connector assembly 350 is intended to be used has particular utility in providing therapy to chronic heart failure patients.

While particular illustrative embodiments have been described, the invention is not intended to be restricted to those embodiments but only by the appended claims. It will be appreciated that those skilled in the art can change or modify the described embodiments, or substitute equivalents for the various elements described and shown, without departing from the scope and spirit of the invention.

What is claimed is:

1. A connector assembly for releasably affixing at least two leads to an implantable medical device, each of the leads comprising a lead body, the connector assembly comprising:
   a single side clamp having first longitudinally bisected channels with first surfaces;
   a support having a side recess and second longitudinally bisected channels with second surfaces, the side recess to receive the side clamp such that the first surfaces are confrontally disposed with the second surfaces to define longitudinally extending ports, the longitudinally extending ports to receive proximal end portions of the at least two lead bodies; and
   a fastener received by the support to urge the side clamp toward the support and to clamp the proximal end portions of the at least two lead bodies between the first surfaces and the second surfaces;
   wherein the side clamp has an outer surface that forms an outer surface of the connector assembly when the side recess receives the side clamp.

2. The connector assembly of claim 1 in which:
the confronting surfaces on the side clamp and the support define at least two ports.

3. The connector assembly of claim 1 in which:
the confronting surfaces comprise confronting channels formed in the side clamp and the support.

4. The connector assembly of claim 1 in which:
the support comprises a molded part.

5. The connector assembly of claim 1 in which:
the side clamp comprises a molded part.

6. The connector assembly of claim 1 in which:
the fastener extends through the side clamp and is threadedly received by the support.

7. The connector assembly of claim 1 in which:
the fastener extends through the side clamp and is threadedly received by an insert carried by the support.

8. The connector assembly of claim 1 further comprising:
a top clamp defining with said support confronting surfaces configured to receive the proximal end portion of an additional lead body, and
a fastener adapted to be received by the support for urging the top clamp toward the support and for clamping the proximal end portion of the additional lead body between the confronting surfaces defined by the top clamp and the support.

9. The connector assembly of claim 2 in which:
the at least two ports have distal ends extending to an outer surface of the connector assembly; and
the confronting surfaces on the side clamp extend to the distal ends of the at least two ports.

10. The connector assembly of claim 1 in which:
the confronting channels are symmetrically disposed about a plane of symmetry.

11. The connector assembly of claim 1 in which:
one of the channels is larger in cross section than the other channel.

12. The connector assembly of claim 6 in which:
the support carries a retainer for inhibiting the removal of the fastener from the support.

13. The connector assembly of claim 12 in which:
the fastener comprises a threaded end including at least one notch extending along the length of the threaded end; and
the retainer has a central opening configured to permit the threaded end of the fastener to be withdrawn through the retainer when the fastener and retainer have a predetermined angular alignment.

14. The connector assembly of claim 12 in which:
the fastener comprises a threaded end; and
the retainer comprises internal threads matching the threads on the fastener end.

15. The connector assembly of claim 12 in which:
the support comprises a molded part and the insert is comolded with the support.

16. An implantable medical device system comprising:
at least two implantable leads, each of the at least two implantable leads comprising a lead body having a proximal end portion carrying at least one electrical terminal, the at least one electrical terminal electrically coupled to the electronic circuitry;
a sealed casing;
the electronic circuitry within the casing, the at least one electrical terminal of the at least two implantable leads electrically coupled to the electronic circuitry; and
a connector assembly attached to the casing to releasably affix the at least two leads, the connector assembly comprising:
at least two receptacles to receive the proximal end portion of the at least two lead bodies, each of the at least two receptacles carrying an electrical contact positioned to engage the at least one electrical terminal, the at least two receptacles comprising a first port and a second port defined by a support and a single side clamp; and
a fastener received by the support to urge the side clamp toward said support and to clamp the proximal end portions of the at least two lead bodies within the first port and the second port;
wherein the single side clamp has first longitudinally bisected channels with first surfaces; and
wherein the support has a side recess and second longitudinally bisected channels with second surfaces, the side recess to receive the side clamp such that the first surfaces are confrontally disposed with the second surfaces to define longitudinally extending ports, the longitudinally extending ports to receive proximal end portions of the at least two lead bodies; and
wherein the side clamp has an outer surface that forms an outer surface of the connector assembly when the side recess receives the side clamp.

17. The implantable medical device system of claim 16 in which:
the first port and the second port are defined by confronting channels in the side clamp and the support.

18. The implantable medical device system of claim 16 in which:
one of the at least two receptacles is configured to receive the proximal end portion of a pacing and/or sensing lead.

19. The implantable medical device system of claim 16 in which:
one of the at least two receptacles is configured to receive the proximal end portion of a cardioverting and/or defibrillating lead.

20. The implantable medical device system of claim 16 in which:
the fastener comprises a screw extending through the side clamp and threadedly received by the support.

21. The implantable medical device system of claim 20 in which:
the support includes a retainer for inhibiting the removal of the fastener from the support when the screw is loosened to release the proximal end portion of the at least two lead bodies.

22. The implantable medical device system of claim 21 in which:

the fastener comprises a threaded end including at least one notch extending along the length of the threaded end; and
the retainer has a central opening configured to permit the threaded end of the fastener to be withdrawn through the retainer when the fastener and retainer have a predetermined angular alignment.

23. The implantable medical device system of claim 21 in which:
the fastener comprises a threaded end; and
the retainer comprises internal threads matching the threads on the fastener end.

24. The implantable medical device system of claim 16 in which:
a top clamp defining with said support confronting surfaces configured to receive the proximal end portion of an additional lead body; and
a fastener adapted to be received by the support for urging the top clamp toward the support and for clamping the proximal end portion of the additional lead body between the confronting surfaces defined by the top clamp and the support.

25. An implantable medical device comprising:
a sealed casing;
an electronic circuitry enclosed within said casing; and
a connector assembly attached to the outside of said casing for releasably affixing at least two leads, each lead comprising a lead body having a proximal end portion carrying at least one electrical terminal and for electrically coupling the at least one electrical terminal to the electronic circuitry, the connector assembly comprising:
a support;
a single side clamp defining with said support confronting surfaces configured to receive the proximal end portion of the lead bodies; and
a fastener received by the support to urge the side clamp toward the support and to clamp the proximal end portions of the lead bodies between said confronting surfaces;
wherein the single side clamp has first longitudinally bisected channels with first surfaces; and
wherein the support has a side recess and second longitudinally bisected channels with second surfaces, the side recess to receive the side clamp such that the first surfaces are confrontally disposed with the second surfaces to define longitudinally extending ports, the longitudinally extending ports to receive proximal end portions of the at least two lead bodies; and
wherein the side clamp has an outer surface that forms an outer surface of the connector assembly when the side recess receives the side clamp.

26. The implantable medical device system of claim 16 in which:
the first port and second port have distal ends extending to an outer surface of connector assembly; and
the confronting channels in the side clamp and the support extend to the distal ends of the first port and second port.

27. The implantable medical device of claim 25 in which:
the confronting surfaces on the side clamp and the support define a first port and a second port;
the first port and the second port have distal ends extending to an outer surface of the connector assembly; and
the confronting surfaces on the side clamp extend to the distal ends of the first port and the second port.

* * * * *